(12) United States Patent
Prevrhal et al.

(10) Patent No.: US 11,506,617 B2
(45) Date of Patent: Nov. 22, 2022

(54) ACTIVE GRATINGS POSITION TRACKING IN GRATINGS-BASED PHASE-CONTRAST AND DARK-FIELD IMAGING

(71) Applicant: KONINKLIJKE PHILIPS N.V., Eindhoven (NL)

(72) Inventors: Sven Peter Prevrhal, Hamburg (DE); Thomas Koehler, Norderstedt (DE); Andriy Yaroshenko, Garching (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/607,084

(22) PCT Filed: Nov. 6, 2020

(86) PCT No.: PCT/EP2020/081218
§ 371 (c)(1),
(2) Date: Oct. 28, 2021

(87) PCT Pub. No.: WO2021/094202
PCT Pub. Date: May 20, 2021

(65) Prior Publication Data
US 2022/0268573 A1 Aug. 25, 2022

(30) Foreign Application Priority Data
Nov. 13, 2019 (EP) .................... 19208885

(51) Int. Cl.
*G01N 23/041* (2018.01)
*A61B 6/00* (2006.01)
*G01B 11/27* (2006.01)

(52) U.S. Cl.
CPC ........... *G01N 23/041* (2018.02); *A61B 6/484* (2013.01); *G01B 11/272* (2013.01); *G01N 2223/32* (2013.01); *G21K 2207/005* (2013.01)

(58) Field of Classification Search
CPC . G01N 23/041; A61B 6/484; G21K 2207/005
See application file for complete search history.

(56) References Cited

U.S. PATENT DOCUMENTS

| 5,812,629 A | 9/1998 | Clauser |
| 2006/0018438 A1 | 1/2006 | Sohal |

(Continued)

FOREIGN PATENT DOCUMENTS

| WO | WO9520139 | 7/1995 |
| WO | WO2014027289 A1 | 2/2014 |
| WO | WO2020054150 A1 | 3/2020 |

OTHER PUBLICATIONS

PCT International Search Report, International application No. PCT/EP2020/081218, dated Dec. 17, 2020.

(Continued)

*Primary Examiner* — Chih-Cheng Kao
(74) *Attorney, Agent, or Firm* — Larry Liberchuk

(57) ABSTRACT

The invention relates to a system and a method for active grating position tracking in X-ray differential phase contrast imaging and dark-field imaging. The alignment of at least one grating positioned in an X-ray imaging device is measured by illuminating a reflection area located on the grating with a light beam, and detecting a reflection pattern of the light beam reflected by the reflection area. The reflection pattern is compared with a reference pattern corresponding to an alignment optimized for X-ray differential phase contrast imaging, and the X-ray imaging device is controlled upon the comparison of the reflection pattern and the reference pattern.

14 Claims, 3 Drawing Sheets

(56) References Cited

U.S. PATENT DOCUMENTS

2014/0126690 A1* 5/2014 Yamaguchi .......... A61B 6/4266
378/36
2015/0216499 A1* 8/2015 Martens ................ A61B 6/587
378/205

OTHER PUBLICATIONS

Millard T.P. et al., "Method for Automatization of the Alignment of a Laboratory based X-Ra Phase Contrast Edge Illumination System", Review of Scientific Instruments, vol. 84, Issue 8, 2013.
Schroter T. et al., "Large-Area Full Field X-Ray Differential Phase-Contrast Imaging Using 2D Tiled Gratings", Journal of Applied Physics D: Applied Physics, vol. 50, No. 22, May 2017, 225401, XP020317435.
Weitkamp T. et al., "X-Ray Phase Imaging with a Grating Interferometer", Optics Express, vol. 13, No. 16, Aug. 2005, pp. 6296-6304.

* cited by examiner

ACTIVE GRATINGS POSITION TRACKING IN GRATINGS-BASED PHASE-CONTRAST AND DARK-FIELD IMAGING

FIELD OF THE INVENTION

The present invention relates to a system for active grating position tracking in X-ray differential phase contrast imaging and dark-field imaging, and a method for active grating position tracking in X-ray differential phase contrast imaging and dark-field imaging.

BACKGROUND OF THE INVENTION

In X-ray interferometry, several gratings are employed that are required to be precisely aligned with respect to each other. Together, they imprint an interference pattern on the X-ray wave front that is disturbed if an object is placed in the field that imparts phase shift and small-angle diffraction. By relatively comparing a measurement of the X-ray field disturbed by the object with a reference measurement without disturbances by the object, phase shift and diffraction images can be obtained that may contain diagnostically relevant information in addition to the conventional attenuation image. Precise positioning of micro-structure X-ray gratings relative to each other is a key requirement for image quality in gratings-based phase-contrast and dark-field interferometry imaging.

If gratings are misaligned either rotationally or translationally around or along either axis, contrast of the interference pattern is diminished or completely suppressed, which reduces image quality. Efforts to mechanically reduce or suppress vibrations and other movement of gratings, for instance caused by thermal changes, have been described. For instance, mechanical isolation from other system components has been attempted. However, this approach fails to entirely mitigate the problem and furthermore introduction of new components increase system complexity and cost.

For these reasons, it would be advantageous to have an X-ray differential phase contrast imaging device that does not suffer from the above mentioned drawbacks.

SUMMARY OF THE INVENTION

It is an object of the present invention to provide a system for active grating position tracking in X-ray differential phase contrast imaging and dark-field imaging with an improved imaging performance.

The object of the present invention is solved by the subject matter of the independent claims, wherein further embodiments are incorporated in the dependent claims.

The described embodiments similarly pertain to the system for active grating position tracking in X-ray differential phase contrast imaging and dark-field imaging, and the method for active grating position tracking in X-ray differential phase contrast imaging and dark-field imaging. Synergetic effects may arise from different combinations of the embodiments although they might not be described in detail.

Further on, it shall be noted that all embodiments of the present invention concerning a method, might be carried out with the order of the steps as described, nevertheless this has not to be the only and essential order of the steps of the method. The herein presented methods can be carried out with another order of the disclosed steps without departing from the respective method embodiment, unless explicitly mentioned to the contrary hereinafter.

According to a first aspect of the invention, there is provided a system for active grating position tracking in X-ray differential phase contrast imaging and dark-field imaging. The system comprises a grating arrangement to be positioned between an X-ray source and an X-ray detector of an X-ray imaging device, wherein the grating arrangement comprises a phase grating and an analyzer grating. The phase grating is arranged between the X-ray source and the analyzer grating, and the analyzer grating is arranged between the phase grating and the X-ray detector. The system further comprises a measurement system for determining an alignment of at least one of the gratings of the grating arrangement: The measurement system comprises a light source configured for generating a light beam, a reflection area located on at least one of the gratings of the grating arrangement, and configured for reflecting the light beam, and a detection device configured for detecting a reflection pattern of the reflected light beam. The system further comprises a processing unit configured for comparing the reflection pattern with a reference pattern, and to control the X-ray imaging device upon the comparison of the reflection pattern and the reference pattern.

The system comprises for example two or three gratings, which are positioned between X-ray source and X-ray detector of an X-ray imaging device. If the positions and their changes are known, correction of their effects may be devised to improve image quality. The source grating may be optional, such that in case of a collimated X-ray source only two gratings can be employed. As it is necessary for a high image quality that the gratings are precisely aligned, the system is configured for precisely measuring an alignment of at least one of the gratings. The system may detect a deviation of the grating from an optimal position and orientation. For that purpose, the system comprises a measurement system with a light source illuminating a reflection area located on the grating. The reflected light beam can be detected by a light detector of the measurement system. A processing unit is configured to compare the direction of light reflected off the respective grating of the source grating, the phase grating and the analyzer grating during operation against a predetermined reference pattern in order to determine whether the alignment of the respective grating is within specifications. If the alignment of the grating is within specifications, the processing unit may trigger the X-ray imaging device to acquire an image. The system for active grating position tracking may, in addition or as an alternative to the X-ray differential phase contrast imaging, further employ X-ray dark field imaging.

In an embodiment of the invention, the light beam is a laser beam.

The laser beam can be precisely focused and offers coherent light. The measurement system may comprise a laser source and a laser detector. It is also possible to use light or laser light of a wide range of the electromagnetic spectrum. Beside of visible light, also infrared light, ultraviolet light or any other kind of coherent or not coherent electromagnetic radiation can be used by the measurement system.

In an embodiment of the invention, the reflection pattern to be detected by the detection device corresponds to a position on the detection device.

A misalignment of the grating due to a shift or a tilt of the reflection area on the grating with respect to a normal position and orientation of the grating can lead in this embodiment of the invention to a change of a position, orientation or shape of the reflection pattern on the light detector. Thus, by detecting the position, orientation or shape of the reflected light beam, the processing unit can derive a change of the translational position and/or the rotational orientation of the respective grating of the source grating, the phase grating and the analyzer grating.

In an embodiment of the invention, the reflection pattern to be detected by the detection device corresponds to a diffraction pattern of the light beam diffracted by the respective grating.

The reflection area reflecting the light beam can also be configured for diffraction of the light beam. Since the microstructure patterns on the gratings also diffracts light, the orientation of the diffraction pattern can also be monitored to determine alignment.

Thus, the light beam is not necessarily a focused beam after reflection, but can comprise information about the reflection area that diffracted the light beam.

In an embodiment of the invention, an orientation of the reflection pattern is used for determining an alignment of the grating.

Detecting an orientation of the reflection pattern of the light beam reflected by the reflection area can provide further information about the alignment of the grating. For example, if interference at the grating is employed, also a rotation of the grating about an axis perpendicular to the reflection area can be detected in this embodiment of the invention.

In an embodiment of the invention, the alignment of the grating corresponds to the position and orientation of the grating.

An alignment of the grating is defined by its position and orientation in space. The measurement of the alignment can be performed in a differential way, by just determining a deviation from a precisely defined position and orientation. In this embodiment of the invention, it might be only necessary to know the alignment of one grating with respect to the other gratings.

In an embodiment of the invention, the reference pattern is acquired with the grating being in an alignment optimized for X-ray differential phase contrast imaging.

A reference pattern of the light beam reflected by the reflection area and illuminating the light detector can be acquired. This reference pattern is taken with the grating being in an aligned condition. Thus, by comparing a reflection pattern with this reference pattern, a deviation of the respective grating from an aligned condition can be detected and estimated.

In an embodiment of the invention, the reflection area on the grating is at least part of a grating structure of the grating.

The reflection area can in this embodiment of the invention be part of the grating structure of the grating. Thus, the grating structure can be used for effecting a diffraction or interference pattern of the reflected light beam.

In an embodiment of the invention, the reflection area on the respective grating is a part of a grating structure of the respective grating.

In addition or as an alternative, also a predetermined reflection area separated from the grating structure can be provided. In this embodiment of the invention, the alternative or additional reflection area is located besides of the grating area of the respective grating. This offers to possibility to provide the reflection area with specific surface structures optimized for the reflection of the light beam.

In an embodiment of the invention, the reflection area on the respective grating is polished.

The reflection area on the respective grating can be polished for enhancing the reflectivity and/or for providing a focused light spot as reflection pattern detected by the detector.

In an embodiment of the invention, the reflection area on the respective grating comprises a structure configured for enhancing a deviation of the reflected light beam from a direction of the reflected light beam with the respective grating being in an aligned condition.

The reflection area can comprise a surface structure, which enhances the deflection of the light beam. For example, a triangular shaped or convex surface can be used. A change of the position of the grating leads in this embodiment of the invention to a shift of the light beam on the reflection area. Moving a nonplanar surface results in a change of the direction of the light beam reflected of the nonplanar surface. Thus, a deviation of the light beam from its normal position is enhanced, and it is also possible to detect a shift of the grating parallel to its surface.

In an embodiment of the invention, the reflection area comprises a first sub area with a first structure and a second sub area with a second structure different from the first structure, wherein the first sub area is configured for effecting a deviation of the reflected light beam with a change in a translational position of the grating, and wherein the second sub area is configured for effecting a deviation of the reflected light beam with a change of an rotational orientation of the grating.

Using two or more separate sub areas with different surface structures enables a more precise detection of shifting and tilting of the grating. In this embodiment, for example, one planar surface can be used for detecting rotations of the grating, and a second nonplanar, structured surface can be used for detecting translations of the grating. However, depending on the direction of translation and the axis of rotation, also different setups can be facilitated. It should be noted that the first sub area and the second sub area can be arranged close to each other. However, the first and second sub area can also be located separate from each other. In this case the reflection area may be divided in two section being apart from each other. The first sub area and the second sub area may also be arranged in an interleaved geometry, e.g. like a chess board with the "white" fields corresponding to the first sub area and the "black" fields corresponding to the second sub area. This interleaved structure is not limited to a chess board structure, but may also include other sub area arrangements.

In an embodiment of the invention, a distance between the reflection area located on the grating and the detection device is configured for enhancing a deviation of the reflection pattern from the reference pattern on the detection device.

By choosing an appropriate distance of the light detector, magnification effects can be used to measure even very small deviations from alignment, as a longer path of the light from the reflection area to the light detector will result in an enhancement of the deviation of the reflection pattern on the light detector from its normal position. The sensitivity of the laser system depends on the length of the distance from the grating to the optical detector. In order to achieve a reasonably compact system, standard optical methods can be used to virtually increase the path length, for instance by using mirrors and dispersing lenses or elements.

In an embodiment of the invention, the system is configured for detecting a deviation from an optimized alignment of the grating and triggering the X-ray imaging device to acquire an X-ray image in phases of expected lower deviation.

The measuring the alignment of the grating by comparing the reflection pattern with the reference pattern can be performed continuously or in pulsed mode. A high frequency of measurements or continuously acquired measurements allow the detection of vibrations of the grating and vibration effects can be mitigated by limiting or triggering imaging exposure to points in time during which gratings alignment is within specifications. It can be also possible to acquire images with the X-ray imaging device during non-perfect alignment, and to correct the acquired data with the knowledge of the vibration amplitude and frequency of the grating.

According to another aspect of the invention, there is provided an X-ray imaging device with active grating position tracking in X-ray differential phase contrast imaging and dark-field imaging, the device comprising (a) an X-ray source, (b) an X-ray detector, (c) a grating arrangement, which is positioned between the X-ray source and the X-ray detector, wherein the grating arrangement comprises a phase grating and an analyzer grating, wherein the phase grating is arranged between the X-ray source and the analyzer grating, and the analyzer grating is arranged between the phase grating and the X-ray detector; (d) a measurement system for determining an alignment of at least one of the gratings of the grating arrangement, wherein the measurement system comprises: a light source configured for generating a light beam, a reflection area located on at least one of the gratings of the grating arrangement, and configured for reflecting the light beam; and a detection device configured for detecting a reflection pattern of the reflected light beam; and (e) a processing unit configured for comparing the reflection pattern with a reference pattern, and to control the X-ray imaging device upon the comparison of the reflection pattern and the reference pattern.

According to another aspect of the invention, there is provided a method for active grating position tracking in X-ray differential phase contrast imaging and dark-field imaging. The method comprises the steps of illuminating a reflection area on a grating of a grating arrangement to be positioned between an X-ray source and an X-ray detector of an X-ray imaging device with a light beam, and detecting a reflection pattern of the light beam reflected by the reflection area. Further, the method comprises the steps of determining an alignment of the grating by comparing the reflection pattern with a reference pattern, and controlling the X-ray imaging device upon the comparison of the reflection pattern and the reference pattern.

The method for active grating position tracking in X-ray differential phase contrast imaging comprises four steps. In the first step, a reflection area on a grating is illuminated with a light source. In the second step, a reflection pattern of the light beam reflected by the reflection area is detected. In the third step, an alignment of the grating by comparing the reflection pattern with a reference pattern is detected. And in the fourth step, the X-ray imaging device is controlled upon the comparison of the reflection pattern and the reference pattern.

Thus, the benefits provided by any of the above aspects equally apply to all of the other aspects and vice versa.

In a gist, the invention relates to a system and a method for active grating position tracking in X-ray differential phase contrast imaging and dark-field imaging. The alignment of at least one grating positioned in an X-ray imaging device is measured by illuminating a reflection area located on the grating with a light beam, and detecting a reflection pattern of the light beam reflected by the reflection area. The reflection pattern is compared with a reference pattern corresponding to an alignment optimized for X-ray differential phase contrast imaging, and the X-ray imaging device is controlled upon the comparison of the reflection pattern and the reference pattern.

The above aspects and embodiments will become apparent from and be elucidated with reference to the exemplary embodiments described hereinafter. Exemplary embodiments of the invention will be described in the following with reference to the following drawings:

DETAILED DESCRIPTION OF EMBODIMENTS

Figure 1:
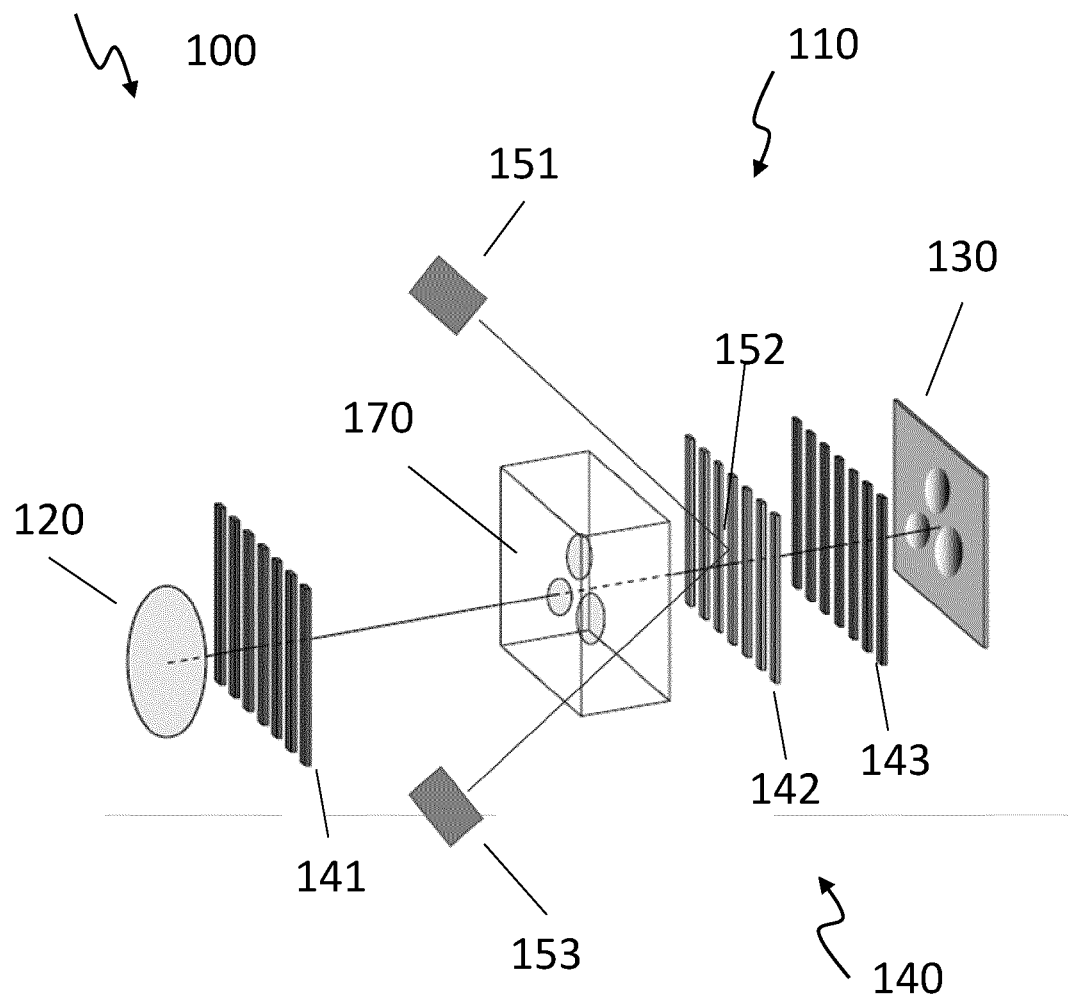
FIG. 1 shows a schematic set-up of a system for active grating position tracking in X-ray differential phase contrast imaging according to an exemplary embodiment of the invention.

FIG. 1 shows a schematic set-up of a system 100 for active grating position tracking in X-ray differential phase contrast imaging according to an exemplary embodiment of the invention. An X-ray source 120 and an X-ray detector 130 of an X-ray imaging device 110 are shown. Between the X-ray source 120 and an X-ray detector 130, a grating arrangement 140 is positioned. The grating arrangement 140 comprises a source grating 141, a phase grating 142 and an analyzer grating 143, in this order from X-ray source 120 to X-ray detector 130. An object to be investigated can be placed between source grating 141 and phase grating 142. A measurement system 150 comprising a light source 151, a reflection area 152 and a light detector 153 is used to measure an alignment of at least one of the gratings. In FIG. 1, the measurement system 150 is configured to measure the alignment of the phase grating 142. The alignment is characterized by the position and orientation of the respective grating with respect to the other gratings, or with respect to the X-ray imaging device 110. A light beam coming from the light source 151 is directed onto the reflection area 152. The reflection area 152 is positioned at the grating, and can be, for example, either directly on the grating structure of the grating itself, or it can be a dedicated area right beside the grating structure on the grating. The reflection area 152 can further comprise an appropriate surface structure. This surface structure can be, for example, polished for optimized specular reflection, or it can be configured for effecting an interference or diffraction pattern of the light beam reflected from the reflection surface 152. It is also possible to shape the surface of the reflection area 152 in a way that a deviation of the direction of the reflected light beam from its normal direction is enhanced when the grating is tilted or shifted with respect to its normal or aligned position. The light reflected from the reflection area 152 is detected by the light detector 153. This detector may be sensitive to the position of the light beam or pattern of the light beam impinging on the surface of the light detector 153. By detecting this reflection pattern of the light beam on the light detector 153, and comparing it with a reference pattern acquired with the grating being in an aligned condition, a deviation of the grating from its aligned position and orientation can be measured.

The reflection area may comprise a first sub area which may allow upon translational movement detection of that translational movement. This can be achieved e.g. by a spherical or other 3D-structured reflection surface. The reflection area may comprise a second sub area which may allow upon rotational movement detection of that rotational movement. This can be achieved e.g. by a plane reflection surface.

A processing unit 160, not shown in FIG. 1, is configured for executing this comparison and for controlling the X-ray imaging device 110 according to the comparison of the reflection pattern with the reference pattern. For example, if the reflection pattern is within the specification, and a deviation from the reference pattern is smaller than a predetermined limit, then the processing unit can trigger the X-ray imaging unit to acquire an image. The processing unit may conduct an image recognition and a computation, in particular if using an interleaved first and second sub area, so as to compute the translational deviation and the rotational deviation. The respective amount of deviation may be computed from the reflection pattern.

Figure 2:
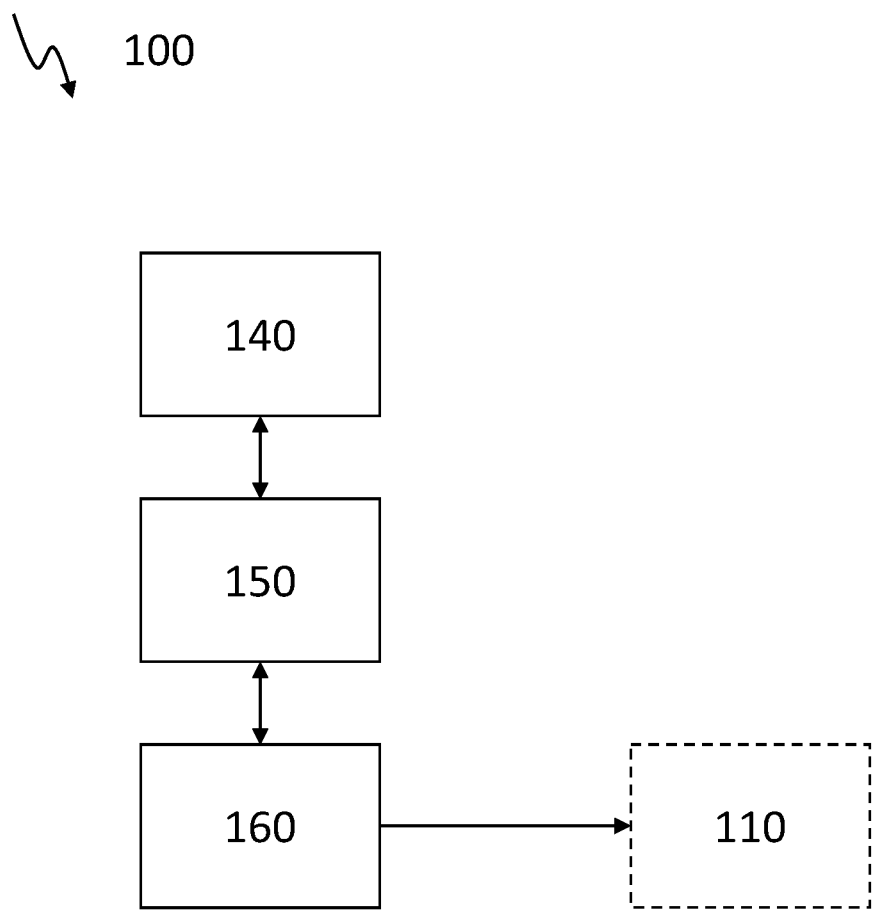
FIG. 2 shows a schematic set-up of a system for active grating position tracking in X-ray differential phase contrast imaging according to another exemplary embodiment of the invention.

FIG. 2 shows a schematic set-up of a system 100 for active grating position tracking in X-ray differential phase contrast imaging according to another exemplary embodiment of the invention. The grating arrangement 140 is in communication with the measurement system 150, as the measurement system 150 measures the position and orientation of a grating of the grating arrangement 140, and the reflection area 152 of the measurement system 150 is positioned on the grating of the grating arrangement 140. The processing unit 160 is in communication with the measurement system, as it may control the light source 151 and reads out the signals of the light detector 153. Further, the processing unit 160 may control the X-ray imaging device 110 by triggering the X-ray source 120 and/or the X-ray detector 130 to acquire an image. The X-ray imaging device 110 is not necessarily a part of the system 100 for active grating position tracking in X-ray differential phase contrast imaging, and therefore depicted in a dashed line.

The processing unit 160 may also include a prediction upon evaluation of previous deviations, in order to e.g. determine a vibration frequency. Based on this prediction, the processing unit may for example activate the X-ray source in periods of low motion gradients, i.e. during max or min amplitudes of a vibration, where the motion gradient is lower than during periods of zero passage. In case the processing unit 160 also determines the amount or quantity of a translational or rotational deviation in real time, the processing unit may provide compensational information by means of which an detected x-ray image is correlated with a compensational factor to provide an image correction in real time.

Figure 3:
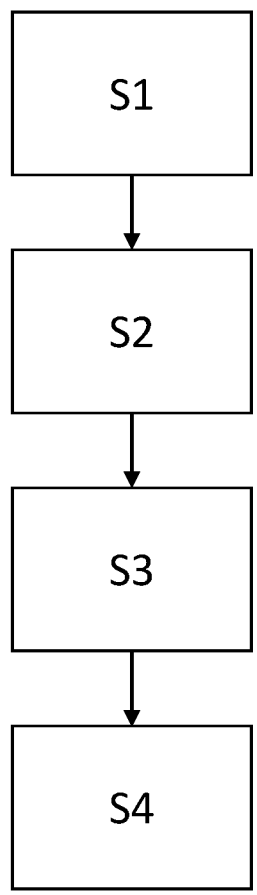
FIG. 3 shows a block diagram of a method for active grating position tracking in X-ray differential phase contrast imaging according to another exemplary embodiment of the invention.

FIG. 3 shows a block diagram of a method for active grating position tracking in X-ray differential phase contrast imaging according to another exemplary embodiment of the invention. In the first step S1, the reflection area 152 on the grating is illuminated by the light source 151. In the second step S2, the reflection pattern of the light beam reflected by the reflection area 152 and impinging onto the light detector 153 is detected. In the third step S3, an alignment of the grating is determined by comparing the reflection pattern with a reference pattern acquired under aligned conditions of the grating. In the fourth step S4, the X-ray imaging device 110 is controlled upon the comparison of the reflection pattern and the reference pattern.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

100 system for active grating position tracking
110 X-ray imaging device
120 X-ray source
130 X-ray detector
140 grating arrangement
141 source grating
142 phase grating
143 analyzer grating
150 measurement system
151 light source
152 reflection area
153 detection device
160 processing unit
170 object

The invention claimed is:

1. A system for active grating position tracking in X-ray differential phase contrast imaging and dark-field imaging, the system comprising:
   a grating arrangement to be positioned between an X-ray source and an X-ray detector of an X-ray imaging device, wherein the grating arrangement comprises
      a phase grating, and
      an analyzer grating, wherein the phase grating is arranged between the X-ray source and the analyzer grating, and the analyzer grating is arranged between the phase grating and the X-ray detector;
   a measurement system for determining an alignment of at least one of the gratings of the grating arrangement, wherein the measurement system comprises:
      a light source configured for generating a light beam;
      a reflection area located on at least one of the gratings of the grating arrangement, and configured for reflecting the light beam; and
      a detector configured for detecting a reflection pattern of the reflected light beam; and
   a processor configured for comparing the reflection pattern with a reference pattern, and to control the X-ray imaging device upon the comparison of the reflection pattern and the reference pattern.

2. The system according to claim 1, wherein the grating arrangement further comprises a source grating, and wherein the source grating is arranged between the X-ray source and the phase grating.

3. The system according to claim 1, wherein the light beam is a laser beam.

4. The system according to claim 1, wherein the reflection pattern to be detected by the detector corresponds to a position on the detector and/or to a diffraction pattern of the light beam diffracted by the respective grating onto which the reflection area is located.

5. The system according to claim 4, wherein an orientation of the reflection pattern is used for determining an alignment of the grating.

6. The system according to claim 1, wherein the alignment of the grating corresponds to the position and orientation of the grating.

7. The system according to claim 1, wherein the reference pattern is acquired with the grating being in an alignment optimized for X-ray differential phase contrast imaging.

8. The system according to claim 1, wherein the reflection area on the respective grating is at least a part of a grating structure of the respective grating.

9. The system according to claim 8, wherein the reflection area on the grating comprises a structure configured for enhancing a deviation of the reflected light beam from a direction of the reflected light beam with the grating being in an aligned condition.

10. The system according to claim 1, wherein the reflection area on the grating is apart from a grating structure of the respective grating, and in particular wherein the reflection area on the grating is polished.

11. The system according to claim 1, wherein the reflection area comprises a first sub area and a second sub area, wherein first sub area has a first structure and the second sub area has a second structure different from the first structure, wherein the first sub area is configured for effecting a deviation of the reflected light beam with a change of a translational position of the respective grating, and wherein the second sub area is configured for effecting a deviation of the reflected light beam with a change of a rotational orientation of the respective grating.

12. The system according to claim 1, wherein a distance between the reflection area located on the respective grating and the detector is configured for enhancing a deviation of the reflection pattern from the reference pattern on the detector.

13. The system according to claim 1, wherein the system is configured for detecting a deviation from an optimized alignment of the grating and triggering the X-ray imaging device to acquire an X-ray image in phases of expected lower deviation.

14. A method for active grating position tracking in X-ray differential phase contrast imaging and dark-field imaging, the method comprising:
   illuminating a reflection area on a grating of a grating arrangement to be positioned between an X-ray source and an X-ray detector of an X-ray imaging device with a light beam;
   detecting a reflection pattern of the light beam reflected by the reflection area;
   determining an alignment of the grating by comparing the reflection pattern with a reference pattern; and
   controlling the X-ray imaging device upon the comparison of the reflection pattern and the reference pattern.

* * * * *